(12) United States Patent
Cebulski et al.

(10) Patent No.: US 9,155,714 B2
(45) Date of Patent: Oct. 13, 2015

(54) COMPOSITIONS COMPRISING AN AROMATIC ALCOHOL AND A TRPV-1 ANTAGONIST, AND USES THEREOF

(71) Applicant: JOHNSON & JOHNSON CONSUMER INC., Skillman, NJ (US)

(72) Inventors: Slawomir Cebulski, Flemington, NJ (US); Michelle Garay, Pittstown, NJ (US); Karien J. Rodriguez, Dunwoody, GA (US); Michael D. Southall, Pennington, NJ (US); Simarna Kaur, Neshanic Station, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 36 days.

(21) Appl. No.: 14/278,007

(22) Filed: May 15, 2014

(65) Prior Publication Data

US 2014/0364418 A1 Dec. 11, 2014

Related U.S. Application Data

(63) Continuation-in-part of application No. 13/911,492, filed on Jun. 6, 2013, now abandoned.

(51) Int. Cl.

| | | |
|---|---|---|
| *A61K 31/085* | (2006.01) | |
| *A61K 31/045* | (2006.01) | |
| *A61K 31/05* | (2006.01) | |
| *A61K 31/55* | (2006.01) | |
| *A61Q 19/10* | (2006.01) | |
| *A61K 8/34* | (2006.01) | |
| *A61K 8/49* | (2006.01) | |
| *A61K 8/60* | (2006.01) | |
| *A61K 31/357* | (2006.01) | |

(52) U.S. Cl.
CPC ............. *A61K 31/085* (2013.01); *A61K 8/34* (2013.01); *A61K 8/4906* (2013.01); *A61K 8/498* (2013.01); *A61K 8/608* (2013.01); *A61K 31/045* (2013.01); *A61K 31/05* (2013.01); *A61K 31/357* (2013.01); *A61K 31/55* (2013.01); *A61Q 19/10* (2013.01)

(58) Field of Classification Search
CPC ........................................................ A61K 31/55
See application file for complete search history.

(56) References Cited

U.S. PATENT DOCUMENTS

| | | | |
|---|---|---|---|
| 5,858,958 | A | 1/1999 | Holzner |
| 8,475,851 | B2 | 7/2013 | Herrmann et al. |
| 2011/0294876 | A1 | 12/2011 | Küper et al. |
| 2011/0305657 | A1 | 12/2011 | Küper et al. |
| 2012/0195870 | A1 | 8/2012 | Herrmann et al. |
| 2012/0201902 | A1 | 8/2012 | Modak et al. |
| 2013/0202543 | A1 | 8/2013 | Küper et al. |
| 2013/0230609 | A1 | 9/2013 | Modak et al. |

FOREIGN PATENT DOCUMENTS

| | | | |
|---|---|---|---|
| WO | WO0067705 | * | 11/2000 |
| WO | WO 2009/087242 A2 | | 7/2009 |
| WO | WO 2009087242 A2 | * | 7/2009 |
| WO | WO 2011/131474 A2 | | 10/2011 |

OTHER PUBLICATIONS

The Honest Company. "Phenoxyethanol." © 2012. Available from: < http://blog.honest.com/what-is-phenoxyethanol/ >.*
EWG Skin Deep Cosmetics Database. "Benzyl alcohol." © 2007. Available from: < http://www.ewg.org/skindeep/ingredient/700697/BENZYL_ALCOHOL/ >.*
"Fragrance material review on phenethyl alcohol." Food and Chemical Toxicology. (2012), vol. 50, pp. 5224-5239.*
The Aromatic Consortium. "Test Plan for Phenethyl Alcohol." © 2002.*
Kueper, T., et al. "Inhibition of TRPV1 for the treatment of sensitive skin." Experimental Dermatology. (2010), vol. 19, pp. 980-986.*
Lee, E., et al. "Comparison of objective and sensory skin irritations of several cosmetic preservatives." Contact Dermatitis. (2007), vol. 56, pp. 131-136.*
Bubble and Bee Organic. "Benzyl Alcohol." © 2009. Available from: < http://chemicaloftheday.squarespace.com/todays-chemical/2009/7/22/benzyl-alcohol.html >.*
EWG's Skin Deep Cosmetics Database. "Phenethyl alcohol." © 2012. Available from: http://www.ewg.org/skindeep/ingredient/704804/PHENETHYL_ALCOHOL/ >.*
Cosmetics Info. "Caprylyl Glycol." © 2013. Available from: < http://cosmeticsinfo.org/ingredient/caprylyl-glycol >.*
Refence MD. "Drug Carriers." (c) 2012. Available from: < http://www.reference.md/files/D004/mD004337.html >.*
Levin, J., et al. "A Guide to the Ingredients and Potential Benefits of Over-The-Counter Cleansers and Moisturizers for Rosacea Patients." J. Clin. Aesthetic Derm. (Aug. 2011), vol. 4, No. 8, pp. 31-49.*
Bagley, D.M. et al., Toxicol in Vitro, 1996, 10(1):1-6.
Bevan, S. et al., Br J Pharmacol, 1992, 107(2):544-552.
Gavva, N.R. et al., J Pharmacol Exp Ther, 2005, 313(1):474-484.
Kueper, T. et al., Exp Dermatol, 2010, 19(11):980-986.
Lee, E. et al., Contact Dermatitis, 2007, Mar:56(3):131-6.
Lin, T.K. et al., J Invest Dermatol, 2013, 133(2):469-478.
Nagy, I. et al., European J of Pharmacol, 500(1-3): 351-369.
Southall, M.D. et al., J Pharmacol Exp Ther, 2003, 304(1):217-222.
Walling, H.W. et al., Clin Cosmet Investig Dermatol, 2010, 3:99-117.
Yosipovitch, G. et al., 2003, Lancet 361(9358):690-694.
Honest Company. "Phenoxyethanol." © 2012 Available from < http://blog, honest.com/what-is-phenoxyethanol/>.
Reference.M.D. "Drug Carriers." © 2012. Available from < http://www.Reference.md/files/D004/mD004337.html >.
"What is Caprylyl Glycol?" © 2012. Available from < http://blog.honest.com/tag/caprylyl-glycol/ >.
International Search Report dated Jul. 31, 2014 for International Application No. PCT/US2014/038295.

* cited by examiner

*Primary Examiner* — Andrew D Kosar
*Assistant Examiner* — John S Kenyon

(57) ABSTRACT

A topical composition providing reduced irritation that contains aromatic alcohols such as phenoxyethanol and a TRPV-1 antagonist is described. The composition is substantially free of parabens. The composition may be used for example for cleansing the skin.

5 Claims, No Drawings

COMPOSITIONS COMPRISING AN AROMATIC ALCOHOL AND A TRPV-1 ANTAGONIST, AND USES THEREOF

CROSS-REFERENCE TO RELATED APPLICATION

This application is a continuation-in-part of U.S. application Ser. No. 13/911,492 filed Jun. 6, 2013, the disclosure of which is hereby incorporated by reference.

FIELD OF THE INVENTION

The present invention relates to a composition comprising an aromatic alcohol and a TRPV-1 antagonist, and methods of use thereof.

BACKGROUND OF THE INVENTION

Phenoxyethanol is a common ingredient used to preserve cosmetic and pharmaceutical formulations for topical administration. Phenoxyethanol, sometimes known as 2-phenoxy-1-ethanol or ethylene glycol monophenyl ether, is a preservative used to provide biocidal activity against various microorganisms. Unfortunately, phenoxyethanol is also an irritant to the skin (see, for example, Lee E et al., *Contact Dermatitis*. 2007 March:56(3):131-6.). Similarly, benzyl alcohol is also known to induce skin irritation in vivo (Bagley, D. M. et al. (1996) *Toxicol In Vitro* 10(1): 1-6).

TRPV-1 (transient receptor potential vanilloid, subfamily V, receptor 1) is a protein encoded by the TRPV-1 gene. TRPV-1 is a non-selective, ligand-gated cation channel that is activated in response to increased temperature and mechanical or chemical stimulus. This receptor is found in the central nervous system as well as in non-neuronal cells, such as keratinocytes. Activation of TRPV-1 allows the transient flux of cations, especially $Ca^{2+}$, into the cell. This $Ca^{2+}$ influx stimulates the sensation of pain and has been associated with the onset of various cellular events such as inflammation. Activation of TRPV-1 is known to induce the release of pro-inflammatory mediators in human keratinocytes (Southall, M. D. et al. (2003) "*J Pharmacol Exp Ther* 304(1): 217-222).

TRPV-1 is known to be activated by capsaicin, a compound found in in chili peppers, and capsazepine is reported to be a TRPV-1 antagonist (Bevan, S. et al., *Br J Pharmacol* 107(2): 544-552). Other compounds known to be TRPV-1 antagonists are (E)-3-(4-t-butylphenyl)-N-(2,3-dihydrobenzo[b][1,4]dioxin-6-yl)acrylamide (Gavva, N. R. et al. (2005) *J Pharmacol Exp Ther* 313(1): 474-484), commercially available as AMG9810 from Tocris Bioscience, Bristol, United Kingdom, and 4-tertiary butyl cyclohexane (Kueper, T. et al. (2010) *Exp Dermatol* 19(11): 980-986), commercially available as SYM-SITIVE 1609 from Symrise GmbH of Holzminden, Germany.

Applicants have now discovered that certain aromatic alcohols including phenoxyethanol activate TRPV-1. This is surprising in that applicants have also found that not all skin irritants activate TRPV-1 and not all topical anti-inflammatory compounds or analgesics inhibit the activation of TRPV-1. Thus, the discovery of the association between aromatic alcohols, their irritating properties, and TRPV-1 is unexpected.

Low irritation, aromatic alcohol-containing topical compositions are provided herein. Advantageously, they also do not require the presence of parabens (esters of para-hydroxybenzoic acid), the effects of which many consumers are concerned about. Further provided are methods of use thereof.

SUMMARY OF THE INVENTION

The invention provides a composition comprising an aromatic alcohol having the formula:

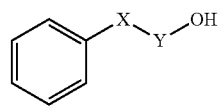

Formula 1 wherein X is an oxygen atom or absent and Y is C1-C2 alkyl; and a TRPV-1 antagonist, wherein said composition is substantially free of esters of para-hydroxybenzoic acid.

The invention also provides a method of cleansing the skin, comprising applying the above composition to the skin and rinsing the composition off of the skin.

The invention further provides a method of reducing irritation induced by topical application of an aromatic alcohol having the formula:

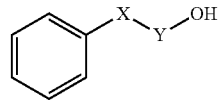

Formula 1 wherein X is an oxygen atom or absent and Y is C1-C2 alkyl; said method comprising topically applying said aromatic alcohol with a TRPV-1 antagonist.

DETAILED DESCRIPTION OF THE INVENTION

Unless defined otherwise, all technical and scientific terms used herein have the meaning commonly understood by one of ordinary skill in the art to which the invention pertains. Also, all publications, patent applications, patents, and other references mentioned herein are incorporated by reference. Unless otherwise indicated, a percentage refers to a percentage by weight (i.e., % (W/W)).

As used herein, "substantially free" of an ingredient means containing less than about 1% by weight, such as less than about 0.5% by weight, such as less than about 0.25% by weight, such as less than about 0.1% by weight of such ingredient. In one embodiment, "substantially free" means completely free of such ingredient.

It is believed that one skilled in the art can, based upon the description herein, utilize the present invention to its fullest extent. The following specific embodiments are to be construed as merely illustrative, and not limiting of the remainder of the disclosure in any way whatsoever.

Aromatic Alcohol

The composition of the invention comprises an aromatic alcohol of Formula I:

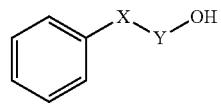

Formula 1 wherein X is an oxygen atom or absent and Y is C1-C2 alkyl.

In one embodiment, the aromatic alcohol is selected from the group consisting of phenoxyethanol, benzyl alcohol, phenethyl alcohol, and mixtures thereof:

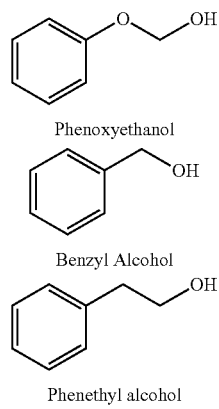

Phenoxyethanol

Benzyl Alcohol

Phenethyl alcohol

The amount of aromatic alcohol in the composition may be varied depending upon factors such as its particular biocidal requirements or whether the composition is "ready-to use," requires dilution with water, or is in the form of a concentrate that will be added to a separate formulation.

Broadly, the composition may contain an amount of aromatic alcohol ranging from about 0.1% to about 80%, or 0.1% to about 66%, such as 0.1% to about 50%, by weight of the composition.

TRPV-1 Antagonist

The composition also includes a TRPV-1 antagonist.

In one embodiment, the TRPV-1 antagonist inhibits the calcium flux of the aromatic alcohol by at least about 12%, or at least about 20%, preferably at least about 50%, such as from about 50% to about 80%, as measured by Calcium Flux Test.

The Calcium Flux Test is performed in the following manner: Recombinant HEK293 cells expressing human vanilloid receptor-1 (TRPV-1; accession number AF196175, EMD Millipore, Billerica, Mass.) are grown in D-MEM/F-12 media (Life Technologies, Grand Island, N.Y.) supplemented with 10% fetal bovine serum, 1% non essential amino acids and 400 μg/mL Geneticin (Gibco, Life Technologies). Cells are plated at a concentration of 15,000 cells per well on poly-D-lysine-coated 384 well plates and incubated overnight at 5% $CO_2$ and 37° C. After incubation, culture media is removed from the wells and replaced with 50 μL per well of Fluo-8 No Wash dye solution (#36315, AAT Bioquest, Sunnyvale, Calif.). The Fluo-8 dye solution is prepared by mixing 20 uL of Fluo-8 NW with 30 mL of 0.33× Pluronic® F127 Plus (BASF of Ludwigshafen, Germany) in assay buffer (1×HBSS+2% of HEPES). Fluo-8 dye is incubated for 30 minutes at room temperature. Intracellular calcium ($Ca^{2+}$) flux is monitored upon exposure to aromatic alcohol in DMSO vehicle by measuring fluorescence intensity at Ex/Em 490/525 on a Functional Drug Screening System (FDSS; Hamamatsu, Germany). Measurements are taken every second for a period of 4 minutes. Results are presented as mean±standard deviation of maximum relative fluorescence units (RFU) during the 4 minute period. Statistical differences are obtained using One Way ANOVA with Tukey Post-hoc test; statistical significance is defined as $P \leq 0.05$.

The Maximum RFU obtained with a given concentration of aromatic alcohol is compared with the Maximum RFU obtained using the same concentration of aromatic alcohol but pretreated with the TRPV-1 antagonist for 5 minutes after dye incubation. Percent inhibition achieved with the TRPV-1 antagonist is calculated as: 100*((Maximum RFU of aromatic alcohol−Maximum RFU of aromatic alcohol pretreated with TRPV-1 antagonist)/Maximum RFU of aromatic alcohol).

Examples of TRPV-1 antagonists include capsazepine, (E)-3-(4-t-butylphenyl)-N-(2,3-dihydrobenzo[b][1,4]dioxin-6-yl)acrylamide (commercially available for example as AMG9810 from Tocris Bioscience, Bristol, United Kingdom), and 4-tertiary butyl cyclohexane (commercially available as SYMSITIVE 1609 from Symrise GmbH of Holzminden, Germany.

Preferably, the TRPV-1 antagonist is 4-tertiary butyl cyclohexane.

The amount of TRPV-1 antagonist in the composition may vary. According to certain embodiments, the amount of TRPV-1 antagonist is from about 0.05% to about 5%, such as from about 0.1% to about 2%, such as from about 0.2% to about 1%, such as from about 0.2% to about 0.5%, by weight of the composition.

The inventors have surprisingly found that TRPV-1 antagonists such as 4-tertiary butyl cyclohexanol are particularly effective at decreasing calcium flux due to aromatic alcohols of Formula I. Accordingly, small amounts of TRPV-1 antagonist may be used in the composition relative to the amount of aromatic alcohol in the composition.

For instance, in certain embodiments when using phenoxyethanol, the mass ratio of TRPV-1 antagonist to aromatic alcohol in the composition may be from about 1:24 to about 1:2.7, such as from about 1:6 to about 1:2.7, such as from about 1:5.4 to about 1:2.7. When using benzyl alcohol, the mass ratio of TRPV-1 antagonist to aromatic alcohol in the composition may be from about 1:0.08 to about 1:0.9. When using phenethyl alcohol, the mass ratio of TRPV-1 antagonist to aromatic alcohol in the composition may be from about 1:0.09 to about 1:3.

Since the amount of 4-tertiary butyl cyclohexanol in SYMSITIVE 1609 is believed to be from about 40% to about 60% (diluted in propylene glycol), when using SYMSITIVE 1609 and phenoxyethanol for example, the mass ratio of 4-tertiary butyl cyclohexanol to aromatic alcohol should be 0.4 to 0.6 times the mass ratios above (i.e., 0.4:24 to 0.6:24, instead of 1:24; 0.4:2.7 to 0.6:2.7, instead of 1:2.7; etc.).

Substantially Free of Parabens

According to certain embodiments, the compositions of the present invention are substantially free of esters of parahydroxybenzoic acid (parabens). Examples of esters of parahydroxybenzoic acid include those having the structure below, wherein R is an alkyl group:

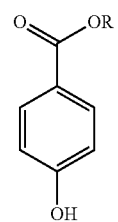

Examples of esters of parahydroxybenzoic acid include methylparaben, ethylparaben, butylparaben, propylparaben, isobutylparaben, heptylparaben, and salts thereof.

Topical Compositions

The compositions of the present invention may include a cosmetically-acceptable topical carrier. The cosmetically-acceptable topical carrier may contain ingredients commonly used, such as water, monoalcohols (such as ethanol and isopropanol); glycols and polyols (such as glycerin, propylene glycol, propanediol, 1,4-butanediol, 1,3-butanediol, 1,2-butanediol, hydroxyethyl urea, sorbitol, sorbitan, xylitol and polyglycerols); glycerin, and combinations thereof. According to certain embodiments, the carrier includes water.

The amount of cosmetically-acceptable topical carrier in the composition may range from about 30% to about 99%, such as from about 40% to about 95%, such as from about 50% to about 95%, such as from about 60% to about 90% by weight of the composition.

In embodiments in which the composition includes a cosmetically-acceptable topical carrier, the amount of aromatic alcohol in such composition may be from about 0.1% to about 5%, such as from about 0.2% to about 2.5%, such as from about 0.3% to about 2%, by weight of the composition.

According to other embodiments the composition is in the form of a concentrate. As such, the composition may consist essentially of aromatic alcohol of Formula I and a TRPV-1 antagonist. For example, the amount of aromatic alcohol in the composition may be from about 55% to about 90%, such as from about 60% to about 85%, such as about 70% to about 85%, by weight of the composition, remainder being TRPV-1 antagonist and optionally up to about 20% of a diluent such as water, a monoalcohol, a glycol/polyol, or combinations thereof.

The compositions of the present invention may include additional ingredients commonly used in topical compositions. Examples of additional ingredients include but are not limited to surfactants/emulsifiers (cationic, anionic, nonionic, and zwitterionic), humectants, emollients and hydrophobic compounds, conditioning agents, opacifying agents, chelating agents, conditioning agents, additional preservatives, skin benefit agents, fragrances, water-soluble or dispersible polymers, and active ingredients (e.g., sunscreens, anti-aging actives, anti-acne actives, and the like).

According to certain embodiments, the composition is aqueous and the pH of the composition is about 6.5 or greater, such as from about 6.5 to about 8.5, such as from about 7.5 to about 8.5.

Compositions of the present invention are particularly suitable for topically applying to skin or mucosa. According to certain embodiments, the composition is used to cleanse the skin or mucosa and may be rinsed therefrom. The composition may be contained within or be in fluid communication with an applicator that is suitable for dispensing it.

According to other embodiments, the invention also provides a method of reducing irritation induced by topical application of an aromatic alcohol of Formula I, said method comprising topically applying said aromatic alcohol with a TRPV-1 antagonist as described above.

EXAMPLE 1

Phenoxyethanol Induces Calcium Flux Via TRPV-1 Receptor

Phenoxyethanol was tested at a series of concentrations in DMSO for activity as a TRPV-1 agonist according to the Calcium Flux Test described above. Capsaicin was used as a positive control.

Maximum RFU values for treatment with phenoxyethanol or capsaisin were compared to the Maximum RFU for a DMSO vehicle alone. The results for phenoxyethanol are shown in Table 1. The results for capsaicin are shown in Table 2. Concentrations of phenoxyethanol and capsaicin are reported in milimolar (mM) and nanomolar (nM), respectively.

Both capsaicin and phenoxyethanol showed dose dependent increases in intracellular calcium flux in TRPV-1-transfected HEK cells. For phenoxyethanol, the increase in Maximum RFU values versus the control vehicle was statistically significant across a wide range of amounts, and increased thirty to forty-fold compared to the vehicle alone. These findings demonstrate activation of the TRPV-1 receptor by phenoxyethanol.

TABLE 1

| Phenoxyethanol (mM) | Maximum RFU (mean ± SD) | ** $P < 0.05$ Compared to Vehicle |
|---|---|---|
| 4 | 453.25 ± 34.18 | ** |
| 3.5 | 404.21 ± 42.32 | ** |
| 3 | 401.68 ± 26.58 | ** |
| 2.5 | 363.73 ± 44.11 | ** |
| 2 | 357.37 ± 44.88 | ** |
| 1.5 | 304.41 ± 70.10 | ** |
| 1 | 200.28 ± 76.93 | ** |
| 0.75 | 124.81 ± 37.58 | n/s |
| 0.5 | 96.96 ± 61.20 | n/s |
| Vehicle | 13.88 ± 2.95 | — | n/s: Not statistically significant
** Statistically significant

TABLE 2

| Capsaicin Concentration (nM) | Maximum RFU (mean ± SD) | ** $P < 0.05$ Compared to Vehicle |
|---|---|---|
| 10000 | 698.83 ± 30.57 | ** |
| 2500 | 617.87 ± 34.14 | ** |
| 625 | 604.13 ± 32.46 | ** |
| 156 | 491.07 ± 21.10 | ** |
| 39 | 405.53 ± 11.25 | ** |
| 10 | 348.17 ± 5.56 | ** |
| 2 | 253.47 ± 24.63 | ** |
| 0.6104 | 121.32 ± 46.41 | ** |
| 0.1526 | 29.34 ± 8.18 | n/s |
| 0.0381 | 10.19 ± 2.94 | n/s |
| Vehicle | 16.23 ± 2.95 | — | n/s: not statistically significant
** statistically significant

EXAMPLE 2

TRPV-1 Antagonists Reduce $Ca^{2+}$ Flux Induced by Phenoxyethanol or Capsaicin

Capsazepine and AMG9810 were tested for activity as TRPV-1 antagonists using the Calcium Flux Test using two different concentrations of phenoxyethanol in DMSO. They were also tested using the Calcium Flux Test in which phenoxyethanol was replaced with capsaicin.

The results are shown in Tables 3-6. Concentrations of capsazepine and AMG9810 are reported in nanomolar (nM).

The results demonstrate that treatment with TRPV-1 antagonists reduces phenoxyethanol-induced calcium flux and capsaicin-induced calcium flux.

TABLE 3

| Capsazepine [nM] | Phenoxyethanol 3 mM | | Phenoxyethanol 2 mM | |
|---|---|---|---|---|
| | Maximum RFU (mean ± SD) | % of Inhibition | Maximum RFU (mean ± SD) | % of Inhibition |
| 10000 | 106.49 ± 4.15 | 75.89 | 79.39 ± 2.79 | 72.34 |
| 2500 | 99.71 ± 6.08 | 77.43 | 84.79 ± 2.68 | 70.46 |
| 625 | 75.71 ± 3.39 | 82.86 | 57.76 ± 2.15 | 79.88 |
| 156 | 101.59 ± 2.44 | 77.00 | 87.54 ± 8.38 | 69.50 |
| 39 | 176.52 ± 75.37 | 60.04 | 75.06 ± 6.64 | 73.85 |
| 10 | 340.96 ± 12.96 | 22.82 | 154.95 ± 19.56 | 46.01 |
| 2 | 486.75 ± 153.02 | — | 236.10 ± 8.91 | 17.73 |
| 0.6104 | 351.36 ± 32.21 | 20.46 | 210.03 ± 46.34 | 26.82 |
| 0.1526 | 508.45 ± 81.79 | — | 319.33 ± 77.43 | — |
| 0 | 441.76 ± 36.68 | — | 287.00 ± 25.75 | — |

TABLE 4

| Capsazepine (nM) | Capsaicin 300 nM | | Capsaicin 100 nM | |
|---|---|---|---|---|
| | Maximum RFU (Mean ± SD) | % of Inhibition | Maximum RFU (Mean ± SD) | % of Inhibition |
| 10000 | 58.73 ± 4.40 | 93.18 | 45.31 ± 14.17 | 93.00 |
| 2500 | 31.08 ± 3.44 | 96.39 | 27.61 ± 4.95 | 95.73 |
| 625 | 28.36 ± 3.16 | 96.71 | 24.39 ± 5.19 | 96.23 |
| 156 | 51.20 ± 14.34 | 94.05 | 29.36 ± 6.46 | 95.46 |
| 39 | 557.38 ± 79.48 | 35.26 | 187.95 ± 177.88 | 70.95 |
| 10 | 771.64 ± 25.92 | 10.37 | 461.29 ± 221.27 | 28.71 |
| 2 | 850.93 ± 28.65 | 1.16 | 665.83 ± 90.25 | — |
| 0 | 860.95 ± 33.14 | — | 647.05 ± 33.18 | — |

TABLE 5

| AMG9810 (nM) | Phenoxyethanol 3 mM | | Phenoxyethanol 2 mM | |
|---|---|---|---|---|
| | Maximum RFU (mean ± SD) | % of Inhibition | Maximum RFU (mean ± SD) | % of Inhibition |
| 10000 | 65.74 ± 4.33 | 70.69 | 59.78 ± 3.84 | 72.37 |
| 2500 | 68.59 ± 4.15 | 69.42 | 58.00 ± 5.34 | 73.19 |
| 625 | 58.16 ± 1.97 | 74.07 | 55.53 ± 8.48 | 74.34 |
| 156 | 75.59 ± 10.97 | 66.29 | 58.21 ± 5.97 | 73.10 |
| 39 | 98.74 ± 23.34 | 55.97 | 165.37 ± 162.35 | 23.57 |
| 10 | 315.60 ± 125.77 | — | 110.26 ± 27.80 | 49.05 |
| 2 | 265.02 ± 52.11 | — | 202.96 ± 18.01 | 6.20 |
| 0.6104 | 405.29 ± 152.93 | — | 189.72 ± 34.94 | 12.32 |
| 0.1526 | 412.30 ± 110.68 | — | 261.54 ± 114.76 | — |
| 0 | 224.26 ± 42.60 | — | 216.39 ± 45.19 | — |

TABLE 6

| AMG9810 (nM) | Capsaicin 300 nM | | Capsaicin 100 nM | |
|---|---|---|---|---|
| | Maximum RFU (mean ± SD) | % of Inhibition | Maximum RFU (mean ± SD) | % of Inhibition |
| 10000 | 44.15 ± 2.20 | 94.95 | 47.00 ± 11.29 | 94.47 |
| 2500 | 78.33 ± 46.56 | 91.05 | 85.41 ± 20.60 | 89.95 |
| 625 | 747.36 ± 77.35 | 14.59 | 735.36 ± 114.75 | 13.45 |
| 156 | 958.56 ± 16.66 | — | 916.79 ± 31.53 | — |
| 39 | 975.35 ± 32.01 | — | 942.69 ± 88.43 | — |
| 0 | 875.05 ± 55.11 | — | 849.62 ± 7.02 | — |

EXAMPLE 3

SYMSITIVE 1609 Reduces $Ca^{2+}$ Flux Induced by Phenoxyethanol or Capsaicin

SYMSITIVE1609 was tested for activity as a TRPV-1 antagonist using the Calcium Flux Test using two different concentrations of phenoxyethanol in DMSO. It was also tested using the Calcium Flux Test in which phenoxyethanol was replaced with capsaicin. The results are shown in Tables 7 and 8, respectively. Concentrations of phenoxyethanol and capsaicin are reported in milimolar (mM) and nanomolar (nM), respectively, but concentrations of SYMSITIVE1609 are reported in % v/v. In Table 7, mass ratios of SYMSITIVE1609 to phenoxyethanol are also reported (molecular weight of phenoxyethanol of 138.16 g/mol, a density of phenoxyethanol of 1.1 g/mL, and a density of SYMSITIVE1609 of 0.95 g/mL).

These results demonstrate that treatment with SYMSITIVE1609 not only reduces phenoxyethanol-induced calcium flux, but is capable of reducing this flux at low ratios of SYMSITIVE1609 to phenoxyethanol.

TABLE 7

| SYMSITIVE 1609 (% v/v) | Phenoxyethanol 3 mM | | | Phenoxyethanol 2 mM | | |
|---|---|---|---|---|---|---|
| | Max RFU (mean ± SD) | % of Inhibition | Ratio (m/m) SYMSITIVE: Phenoxyethanol | Max RFU (mean ± SD) | % of Inhibition | Mass Ratio SYMSITIVE: Phenoxyethanol |
| 0.04839 | 52.56 ± 6.41 | 79.62 | 1:0.9 | 48.89 ± 4.25 | 72.44 | 1:0.6 |
| 0.01613 | 49.86 ± 5.59 | 80.67 | 1:2.7 | 52.45 ± 2.42 | 70.44 | 1:1.8 |
| 0.00538 | 73.49 ± 11.30 | 71.51 | 1:8 | 55.66 ± 2.52 | 68.63 | 1:5.4 |
| 0.00179 | 200.63 ± 15.30 | 22.22 | 1:24 | 137.07 ± 9.64 | 22.75 | 1:16 |
| 0.00060 | 263.43 ± 3.66 | — | 1:73 | 190.00 ± 48.44 | — | 1:48.7 |
| 0 | 257.93 ± 39.06 | — | — | 177.43 ± 19.36 | — | — |

TABLE 8

| SYMSITIVE1609 (% v/v) | Capsaicin 100 nM | | |
|---|---|---|---|
| | Maximum RFU (mean ± SD) | % of Inhibition | |
| 0.04839 | 707.54 ± 269.73 | 29.73 | |
| 0.01613 | 713.35 ± 621.33 | 29.15 | |
| 0.00538 | 1119.65 ± 140.29 | — | |
| 0.00179 | 1293.49 ± 40.06 | — | |
| 0.00060 | 1305.23 ± 33.35 | — | |
| 0 | 1006.91 ± 74.51 | — | |

EXAMPLE 4

Preparation of Formulated Cleansing Compositions

A comparative cleansing composition (Comparative Example C1) was prepared using the ingredients listed in Table 9:

TABLE 9

Comparative Example, C1

| Trade name | INCI Name | % wt |
|---|---|---|
| Deionized Water | Water | 79.9 |
| Texapon N70A | Sodium Lauryl Sulfate | 3.7 |
| Tween 28-LQ | PEG-80 Sorbitan Laurate | 5.0 |
| Miranol HMD | Sodium Lauroamphoacetate | 2.0 |
| TegoBetain L7V | Cocamidopropyl Betain | 6.4 |
| Phenoxetol | Phenoxyethanol | 2.0 |
| Hydrolite CG | Caprylyl Glycol | 1.0 |
| Citric Acid (50% solution) | Citric Acid | q.s |

The composition shown in Table 9 above was prepared as follows. Water was added to a glass beaker and heated to 60° C. Texapon N70A was mixed in until fully dissolved. While mixing, Tween 28-LQ, Miranol HMD and TegoBetain L7V were added and mixing was continued until the mixture was clear. Hydrolite CG and Phenoxetol were added at the same time and mixing was continued while slowly lowering the temperature to room temperature. pH was adjusted to a target of 5.6 using citric acid.

Another comparative cleansing composition, Comparative Example C2, was prepared using the ingredients listed in Table 10:

TABLE 10

Comparative Example, C2

| Trade name | INCI Name | % wt |
|---|---|---|
| Deionized Water | Water | 80.9 |
| Texapon N70A | Sodium Lauryl Sulfate | 3.7 |
| Tween 28-LQ | PEG-80 Sorbitan Laurate | 5.0 |
| Miranol HMD | Sodium Lauroamphoacetate | 2.0 |
| TegoBetain L7V | Cocamidopropyl Betain | 6.4 |
| Phenoxetol | Phenoxyethanol | 2.0 |
| Citric Acid (50% solution) | Citric Acid | q.s - pH adjuster |

The composition shown in Table 10 was prepared as follows. Water was added to a glass beaker and heated to 60° C. Texapon N70A was mixed in until fully dissolved. While mixing, Tween 28-LQ, Miranol HMD and TegoBetain L7V were added and mixing was continued until the mixture was clear. Phenoxetol was added at the same time and mixing was continued while slowly lowering the temperature to room temperature. pH was adjusted to a target of 5.6 using citric acid.

A composition according the invention, Composition E1, was prepared using the ingredients shown in Table 11.

TABLE 11

Inventive Example, E1

| Trade Name | INCI Name | % wt |
|---|---|---|
| Deionized Water | Water | 81.9 |
| Texapon N70A | Sodium Lauryl Sulfate | 3.7 |
| Tween 28-LQ | PEG-80 Sorbitan Laurate | 5.0 |
| Miranol HMD | Sodium Lauroamphoacetate | 2.0 |
| TegoBetain L7V | Cocamidopropyl Betain | 6.4 |
| Phenoxetol | Phenoxyethanol | 2.0 |
| Hydrolite CG | Caprylyl Glycol | 1.0 |
| SymSitive 1609 | trans-4-tert-butylcyclohexanol | 1.0 |
| Citric Acid (50% solution) | Citric Acid | q.s |

The composition shown in Table 11 was prepared as follows. Water was added to a glass beaker and heated to 60° C. Texapon N70A was mixed in until fully dissolved. While mixing, Tween 28-LQ, Miranol HMD and TegoBetain L7V were added and the mixing was continued until the mixture was clear. Hydrolite CG, Phenoxetol, and SYMSITIVE1609 were then added at the same time and mixing was continued while slowly lowering the temperature to room temperature. pH was adjusted to the target of 5.6 using citric acid.

EXAMPLE 5

Inventive Example, E1 Reduces $Ca^{2+}$ Flux Compared with Comparative Example, C1

The compositions of Comparative Examples C1 and C2 were tested for calcium flux levels using the Calcium Flux Test. The results are shown in Table 12, and demonstrate that formulated cleansing compositions including phenoxyethanol (with or without additional preservative caprylyl glycol) induce calcium flux.

TABLE 12

| | Comparative Example, C1 | | Comparative Example, C2 | |
|---|---|---|---|---|
| Cleanser (% v/v) | Maximum RFU (mean ± SD) | **P < 0.05 Compared to Vehicle | Maximum RFU (mean ± SD) | **P < 0.05 Compared to Vehicle |
| 0.125 | 129.62 ± 29.43 | ** | 146.97 ± 23.41 | ** |
| 0.0625 | 80.34 ± 14.75 | ** | 72.05 ± 8.81 | ** |
| 0.0313 | 40.66 ± 7.89 | n/s | 33.42 ± 8.32 | n/s |
| 0.0156 | 27.36 ± 4.73 | n/s | 18.51 ± 1.09 | n/s |
| Vehicle (Cleanser with no phenoxyethanol) | 34.60 ± 5.58 | — | — | — | n/s: Not statistically significant
** Statistically significant

Inventive Example, E1 was also tested using the Calcium Flux Test. The results are shown in Table 13 and compared against the results for Comparative Example C1, reproduced from Table 12.

These results demonstrate that inclusion of SYMSI-TIVE1609 in a cleansing formulation with phenoxyethanol inhibits calcium flux caused by the phenoxyethanol in a manner that increases with the amount of the cleansing formulation.

TABLE 13

| | Comparative Example, C1 | Inventive Example, E1 | |
| --- | --- | --- | --- |
| Cleanser (% v/v) | Maximum RFU (mean ± SD) | Maximum RFU (mean ± SD) | % of Inhibition |
| 0.0625 | 80.34 ± 14.75 | 29.23 ± 5.77 | 63.62 |
| 0.03125 | 40.66 ± 7.89 | 17.67 ± 4.68 | 56.54 |
| 0.01563 | 27.36 ± 4.73 | 12.44 ± 2.63 | 54.54 |
| 0.00781 | 19.04 ± 11.59 | 13.72 ± 2.29 | 27.94 |
| 0.00391 | 22.35 ± 3.21 | 13.85 ± 2.96 | 38.04 |
| 0.00195 | 34.38 ± 4.23 | 31.02 ± 4.57 | 9.76 |
| 0.00098 | 39.83 ± 1.83 | 45.16 ± 1.95 | — |

EXAMPLE 6

Hydrocortisone, Diphenhydramine or Lidocaine do not Reduce Phenoxyethanol-Induced Calcium Flux in TRPV-1 Expressing Cells The analgesics hydrocortisone, diphenhydramine and lidocaine, all of which have been shown to be effective at reducing neurosensory responses, such as itch and sting (see Lin, T. K. et al. (2013) *J Invest Dermatol* 133(2): 469-478; Yosipovitch, G. et al. (2003) *Lancet* 361(9358): 690-694; and Walling, H. W. et al. (2010) *Clin Cosmet Investig Dermatol* 3: 99-117) were tested using the Calcium Flux Test. The results are shown in Table 14.

TABLE 14

| Compound | Phenoxyethanol 3 mM Maximum RFU (Mean ± SD) | Phenoxyethanol 2 mM Maximum RFU (Mean ± SD) | Capsaicin 300 nM Maximum RFU (Mean ± SD) |
| --- | --- | --- | --- |
| Hydrocortisone 100 μM | 225.19 ± 38.09 | 160.66 ± 30.14 | 963.83 ± 65.21 |
| Hydrocortisone 25 μM | 309.90 ± 40.00 | 171.65 ± 83.27 | 950.97 ± 49.52 |
| Diphenhydramine 100 μM | 195.47 ± 53.34 | 141.61 ± 33.91 | 825.37 ± 9.95 |
| Diphenhydramine 25 μM | 312.62 ± 67.77 | 158.25 ± 0.69 | 899.35 ± 10.60 |
| Lidocaine 100 μM | 205.92 ± 16.97 | 116.25 ± 25.92 | n/d |
| Lidocaine 25 μM | 197.45 ± 41.14 | 124.96 ± 22.24 | n/d |
| Vehicle | 216.86 ± 36.93 | 155.87 ± 46.55 | 896.85 ± 16.71 | n/d = not determined

The results show that none of hydrocortisone, diphenhydramine or lidocaine were effective at reducing phenoxyethanol-induced calcium flux in TRPV-1-expressing HEK293 cells. Thus, not all analgesic agents are TRPV-1 antagonists.

EXAMPLE 7

Irritants Such as Sodium Bicarbonate do not Induce Calcium Flux in TRPV-1 Expressing Cells Benzyl alcohol and sodium bicarbonate were tested using the Calcium Flux Test. Both of these compounds are known to induce skin irritation in vivo (Bagley, D. M. et al. (1996) *Toxicol In Vitro* 10(1): 1-6.) The results are shown in Table 15.

TABLE 15

| Benzyl Alcohol (mM) | Maximum RFU (mean ± SD) | **$P < 0.05$ Compared to Vehicle | Sodium Bicarbonate (mM) | Maximum RFU (mean ± SD) | **$P < 0.05$ Compared to Vehicle |
| --- | --- | --- | --- | --- | --- |
| 4 | 362.51 ± 126.09 | ** | 0.5 | 3.39 ± 2.66 | n/s |
| 2 | 135.45 ± 12.15 | n/s | 0.25 | 124.90 ± 8.41 | ** |
| 1 | 113.51 ± 4.70 | n/s | 0.125 | 114.34 ± 6.46 | n/s |
| 0.5 | 104.45 ± 12.50 | n/s | 0.0625 | 102.15 ± 4.19 | n/s |
| 0.25 | 64.45 ± 28.15 | n/s | 0.03125 | 109.99 ± 1.37 | n/s |
| Vehicle | 101.19 ± 2.56 | — | Vehicle | 98.80 ± 12.93 | — | n/s: Not statistically significant
** Statistically significant

In this test, benzyl alcohol did not show statistically significant activity for TRPV-1 activation at doses of 2 mM and below. However, as shown in Example 9, benzyl alcohol does exhibit such activity at lower doses as well. The difference in results may arise from optimization of the test method to lower the background readings (the vehicle alone was approximately 9 RFU in Example 9, Table 19, versus approximately 101 RFU in Table 15 above), resulting in higher sensitivity of the assay showing statistically significant changes for the lower doses of benzyl alcohol.

These results also demonstrate that not all skin irritants, i.e., sodium bicarbonate, activate TRPV-1.

EXAMPLE 8

Additional Inventive Examples

A composition according to the invention, Composition E2, is prepared by blending the ingredients listed in Table 16:

TABLE 16

| Inventive Example E2 | | |
| --- | --- | --- |
| Trade Name | INCI Name | % wt |
| Deionized Water | Water | 82.8 |
| Texapon N70A | Sodium Lauryl Sulfate | 3.7 |

TABLE 16-continued

Inventive Example E2

| Trade Name | INCI Name | % wt |
|---|---|---|
| Tween 28-LQ | PEG-80 Sorbitan Laurate | 5.0 |
| Miranol HMD | Sodium Lauroamphoacetate | 2.0 |
| TegoBetain L7V | Cocamidopropyl Betain | 6.4 |
| Phenoxetol | Phenoxyethanol | 2.0 |
| Hydrolite CG | Caprylyl Glycol | 1.0 |
| SymSitive 1609 | trans-4-tert-butylcyclohexanol | 0.1 |
| Citric Acid (50% solution) | Citric Acid | q.s |

The composition shown in Table 16 above is prepared as follows. Water is added to a glass beaker and heated to 60° C. Texapon N70A is mixed in until fully dissolved. While mixing, Tween 28-LQ, Miranol HMD and TegoBetain L7V are added and mixing is continued until the mixture is clear. Hydrolite CG, Phenoxetol, and SYMSITIVE1609 are then added at the same time and mixing is continued while slowly lowering the temperature to room temperature. pH is adjusted to the target of 5.6 using citric acid.

A composition according to the invention, Composition E3, is prepared by blending the ingredients listed in Table 17:

TABLE 17

Inventive Example, E3

| Trade Name | INCI Name | % wt |
|---|---|---|
| Purified Water | Water | 86.95 |
| Carbomer | Cross-linked polyacrylic acid | 0.60 |
| VERSENE NA | Disodium EDTA | 0.20 |
| Dimethicone | Dow Corning Q7-9120 Silicone | 5.0 |
| Brij 72 | Steareth-2 | 0.75 |
| Brij 721 | Steareth-21 | 1.50 |
| Finsolv TN | C12-15 Alkyl Benzoate | 2.0 |
| Phenoxetol | Phenoxyethanol | 2.0 |
| SymSitive 1609 | trans-4-tert-butylcyclohexanol | 1.0 |

The composition shown in Table 17 is prepared as follows. An oil phase is prepared by adding C 12-15 alkyl benzoate to a clean glass beaker. Agitation is begun and the vessel is heated to 55-60° C. When the oil phase reaches 55° C. or higher, Brij 72, Brij 721 and SYMSITIVE1609 are added. When the oil phase reaches 55-60° C., it is held at that temperature and mixed for 15 min (or until uniform). The temperature is then held at 55-60° C. with mixing until addition to water phase.

A water phase is prepared by adding water to a clean glass beaker. Agitation is begun and the vessel is heated to 55-60° C. Disodium EDTA is added. At 55-60° C., the ingredients are mixed for 15 min or until homogeneous. The temperature is then held at 55-60° C. with mixing for phasing. The oil phase is added to the water phase with increased agitation and then mixed at high speed for 10-20 min. At 50° C. or lower, dimethicone is added. At 40° C. or lower, Phenoxetol is added. The phases are then mixed for 10 min or until uniform. Sodium hydroxide is added (target pH was 5.4). The composition is then mixed for 10 min or until uniform. This is mixed until uniform. Water is then added to QS and the composition was then mixed for 10 minutes.

A composition according to the invention is prepared by blending the ingredients listed in Table 18:

TABLE 18

Inventive Example, E4

| Trade Name | INCI Name | wt % |
|---|---|---|
| Deionized Water | Water | 69.04 |
| Sodium Chloride | Sodium Chloride | 0.01 |
| Hydrolite CG | Caprylyl Glycol | 1.0 |
| SymSitive 1609 | trans-4-tert-butylcyclohexanol | 1.0 |
| Snow White Petrolatum | Petrolatum | 4.00 |
| Isofol 28 | Dodecylhexadecanol | 2.50 |
| Dow Corning Q7-9120 (20 CS) | Dimethicone | 1.25 |
| Kessco IPP | Isopropyl Palmitate | 3.00 |
| Varisoft TA-100 | Distearyldimonium Chloride | 5.00 |
| Glycerin | Glycerin | 12.00 |
| Phenoxetol | Phenoxyethanol | 1.0 |

The composition shown in Table 8 is prepared as follows. Water is added to a process vessel. Mixing is begun and salt is added and mixed until dissolved. Heat is applied and mixing continued until to 85° C. is reached. Varisoft TA 100 is added, as is petrolatum and Isofol 28, DC Q7-9120 20 cs., and isopropyl palmitate. The composition is mixed at 85° C. for another 10-15 minutes. The composition is then removed from heat, mixed again and cooled. At 40° C., Phenoxetol and SYMSITIVE 1609 are added, and then the sample is q.s. with water and continued to mix and cool to 30-35° C.

EXAMPLE 9

Benzyl Alcohol and Phenethyl Alcohol Induce Calcium Flux Via TRPV-1 Receptor

Benzyl alcohol and phenethyl alcohol were tested at a series of concentrations in DMSO for activity as a TRPV-1 agonist as described in Example 1. The results are shown in Table 19. Concentrations of benzyl alcohol and phenethyl alcohol are reported in units of % w/v.

Both benzyl alcohol and phenethyl alcohol showed dose dependent increases in intracellular calcium flux in TRPV-1-transfected HEK cells. For both compounds, the increase in Maximum RFU values versus the control vehicle was statistically significant across a wide range of amounts. These findings demonstrate activation of the TRPV-1 receptor by benzyl alcohol and phenethyl alcohol.

TABLE 19

| Benzyl Alcohol (% w/v) | Maximum RFU (mean ± SD) |
|---|---|
| 0.04 | 608.23 ± 10.21 |
| 0.013072 | 160.8 ± 12.61 |
| 0.004357 | 43.91 ± 3.74 |
| 0.001452 | 19.94 ± 3.08 |
| 0.000484 | 15.75 ± 1.8 |
| 0.000161 | 10.95 ± 0.23 |
| 5.38E−05 | 13.23 ± 6.33 |
| 1.79E−05 | 10.17 ± 1.19 |
| 5.98E−06 | 7.25 ± 0.71 |
| 1.99E−06 | 9.36 ± 0.52 |
| 6.64E−07 | 9.37 ± 1.66 |
| 0 | 9.54 ± 1.6 |

TABLE 20

| Phenethyl Alcohol (% w/v) | Maximum RFU (mean ± SD) |
|---|---|
| 0.12 | 755.2 ± 12.89 |
| 0.04 | 548.5 ± 37.22 |
| 0.013 | 185.92 ± 28.6 |
| 0.0044 | 70.4 ± 31.61 |
| 0.0015 | 25.95 ± 0.85 |
| 0.00048 | 14.41 ± 3.06 |
| 0.00016 | 10.14 ± 4.39 |
| 0.000054 | 8.66 ± 0.82 |
| 0.000018 | 10.71 ± 2.34 |
| 0.000006 | 7.99 ± 1.93 |
| 0.000002 | 12.8 ± 1.35 |
| 0 | 12.89 ± 1.79 |

EXAMPLE 10

Capsazepine Reduces $Ca^{2+}$ Flux Induced by Benzyl Alcohol

Capsazepine was tested for activity as a TRPV-1 antagonist with different concentrations of benzyl alcohol in DMSO as described in Example 2.

The results are shown in Tables 21 and 22.

The results demonstrate that treatment with a TRPV-1 antagonist reduces benzyl alcohol-induced calcium flux.

TABLE 21

| Benzyl Alcohol (% w/v) | 10 uM Capsazepine Max RFU | without Capsazepine Max RFU | % Inhibition |
|---|---|---|---|
| 0.04 | 18.82 | 410.41 | 95.41% |
| 0.013072 | 10.48 | 93.35 | 88.78% |
| 0.004357 | 8.14 | 31.54 | 74.18% |
| 0.001452 | 11.63 | 14.03 | — |
| 0.000484 | 8.17 | 11.38 | — |
| 0.000161 | 7.95 | 8.44 | — |
| 0.0000538 | 10.90 | 5.38 | — |
| 0.0000179 | 8.92 | 4.38 | — |
| 0.00000598 | 9.46 | 4.25 | — |
| 0.00000199 | 11.32 | 3.07 | — |
| 6.64E-07 | 11.79 | 7.66 | — |
| 0 | 13.30 | 3.65 | — |

TABLE 22

| Benzyl Alcohol (% w/v) | 10 uM Capsazepine Maximum RFU (mean ± SD) | without Capsazepine Maximum RFU (mean ± SD) | % Inhibition |
|---|---|---|---|
| 0.04 | 28.72 ± 1.5 | 424.01 ± 2.92 | 93.23% |
| 0.013072 | 21.7 ± 0.2 | 124.54 ± 13.18 | 82.58% |
| 0.004357 | 15.33 ± 1 | 55.75 ± 2.68 | 72.51% |
| 0.001452 | 15.7 ± 2.1 | 30.81 ± 0.98 | — |
| 0.000484 | 17.15 ± 1.46 | 25.83 ± 5.34 | — |
| 0.000161 | 19.83 ± 3.44 | 16.17 ± 1.16 | — |
| 0.0000538 | 18.44 ± 0.07 | 17.1 ± 3.42 | — |
| 0.0000179 | 18.21 ± 2.76 | 17.05 ± 0.19 | — |
| 0.00000598 | 16.77 ± 1.48 | 17.82 ± 0.88 | — |
| 0.00000199 | 18.74 ± 2.18 | 18 ± 3.24 | — |
| 6.64E-07 | 18.24 ± 2.53 | 13.85 ± 1.83 | — |
| 0 | 18.24 ± 1.3 | 16.68 ± 0.16 | — |

EXAMPLE 11

Capsazepine Reduces $Ca^{2+}$ Flux Induced by Phenethyl Alcohol

Capsazepine was tested for activity as a TRPV-1 antagonist with different concentrations of phenethyl alcohol in DMSO as described in Example 2.

The results are shown in Tables 23 and 24.

The results demonstrate that treatment with a TRPV-1 antagonist reduces phenethyl alcohol-induced calcium flux.

TABLE 23

| Phenethyl Alcohol (% w/v) | 10 uM Capsazepine Max RFU | without Capsazepine Max RFU | |
|---|---|---|---|
| 0.12 | 345.95 | 605.31 | 42.85% |
| 0.04 | 26.42 | 441.18 | 94.01% |
| 0.013 | 4.56 | 123.10 | 96.30% |
| 0.0044 | 11.56 | 26.36 | 56.15% |
| 0.0015 | 11.68 | 8.68 | — |
| 0.00048 | 11.71 | 10.59 | — |
| 0.00016 | 11.64 | 7.21 | — |
| 0.000054 | 6.90 | 7.70 | — |
| 0.000018 | 13.60 | 5.43 | — |
| 0.000006 | 13.70 | 5.48 | — |
| 0.000002 | 12.76 | 6.43 | — |
| 0 | 13.44 | 11.50 | — |

TABLE 24

| Phenethyl Alcohol (% w/v) | 10 uM Capsazepine Maximum RFU (mean ± SD) | without Capsazepine Maximum RFU (mean ± SD) | |
|---|---|---|---|
| 0.12 | 364.66 ± 13.76 | 580.44 ± 3.06 | 37.18% |
| 0.04 | 39.89 ± 5.81 | 470.23 ± 7.11 | 91.52% |
| 0.013 | 12.32 ± 3.27 | 200.02 ± 6.15 | 93.84% |
| 0.0044 | 15.66 ± 0.4 | 79.18 ± 0.23 | 80.22% |
| 0.0015 | 18.5 ± 0.5 | 40.5 ± 0.05 | 54.32% |
| 0.00048 | 20.58 ± 0.6 | 31.36 ± 3.52 | — |
| 0.00016 | 19.48 ± 0.51 | 22.15 ± 0.76 | — |
| 0.000054 | 21.47 ± 3.93 | 21.75 ± 4.01 | — |
| 0.000018 | 18.18 ± 0.59 | 17.58 ± 0.7 | — |
| 0.000006 | 18 ± 0.75 | 17.74 ± 1.46 | — |
| 0.000002 | 18.03 ± 3.35 | 12.28 ± 3.52 | — |
| 0 | 17.46 ± 0.4 | 17.98 ± 0.83 | — |

EXAMPLE 12

SYMSITIVE 1609 Reduces $Ca^{2+}$ Flux Induced by Benzyl Alcohol

SYMSITIVE1609 was tested for activity as a TRPV-1 antagonist as described in Example 3 with different concentrations of benzyl alcohol in DMSO. The results are shown in Table 25. Concentrations of benzyl alcohol are reported in % w/v but concentrations of SYMSITIVE1609 are reported in % v/v.

TABLE 25

| Benzyl Alcohol (% w/v) | 0.05% v/v Symsitive Maximum RFU (mean ± SD) | without Symsitive Maximum RFU (mean ± SD) | % Inhibition |
|---|---|---|---|
| 0.04 | 76.89 ± 8.55 | 608.23 ± 10.21 | 87.36% |
| 0.013072 | 33.14 ± 3.51 | 160.8 ± 12.61 | 79.39% |
| 0.004357 | 29.71 ± 0.46 | 43.91 ± 3.74 | 32.33% |
| 0.001452 | 24.12 ± 2.33 | 19.94 ± 3.08 | — |
| 0.000484 | 25.7 ± 1.62 | 15.75 ± 1.8 | — |
| 0.000161 | 30.72 ± 1.65 | 10.95 ± 0.23 | — |
| 0.0000538 | 27.91 ± 0.47 | 13.23 ± 6.33 | — |
| 0.0000179 | 25.07 ± 1.14 | 10.17 ± 1.19 | — |
| 5.98E−06 | 25.56 ± 1.86 | 7.25 ± 0.71 | — |
| 1.99E−06 | 20.27 ± 6.14 | 9.36 ± 0.52 | — |
| 6.64E−07 | 24.22 ± 2.38 | 9.37 ± 1.66 | — |
| 0 | 23.1 ± 1.61 | 9.54 ± 1.6 | — |

EXAMPLE 13

SYMSITIVE 1609 Reduces $Ca^{2+}$ Flux Induced by Phenethyl Alcohol

SYMSITIVE1609 was tested for activity as a TRPV-1 antagonist as described in Example 3 with different concentrations of phenethyl alcohol in DMSO. The results are shown in Table 26. Concentrations of phenethyl alcohol are reported in % w/v but concentrations of SYMSITIVE1609 are reported in % v/v.

TABLE 26

| Phenethyl Alcohol (% w/v) | 0.05% v/v Symsitive Maximum RFU (mean ± SD) | without Symsitive Maximum RFU (mean ± SD) | % Inhibition |
|---|---|---|---|
| 0.12 | 464.85 ± 56.24 | 755.2 ± 12.89 | 38.45% |
| 0.04 | 92.46 ± 21.67 | 548.5 ± 37.22 | 83.14% |
| 0.013 | 19 ± 2.48 | 185.92 ± 28.6 | 89.78% |
| 0.0044 | 25.22 ± 2.31 | 70.4 ± 31.61 | 64.17% |
| 0.0015 | 27.46 ± 5.12 | 25.95 ± 0.85 | — |
| 0.00048 | 27.05 ± 1.28 | 14.41 ± 3.06 | — |
| 0.00016 | 25.21 ± 1.56 | 10.14 ± 4.39 | — |
| 0.000054 | 26.05 ± 0.64 | 8.66 ± 0.82 | — |
| 0.000018 | 21.02 ± 0.79 | 10.71 ± 2.34 | — |
| 0.000006 | 17.15 ± 5.43 | 7.99 ± 1.93 | — |
| 0.000002 | 18.15 ± 2.97 | 12.8 ± 1.35 | — |
| 0 | 21.77 ± 1.8 | 12.89 ± 1.79 | — |

What is claimed is:

1. A method of reducing irritation induced by topical application of an aromatic alcohol having the formula:

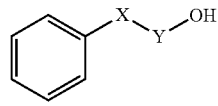

wherein X is an oxygen atom or absent and Y is C1-C2 alkyl; said method comprising topically applying said aromatic alcohol with a TRPV-1 antagonist.

2. The method of claim 1, wherein said aromatic alcohol is selected from the group consisting of phenoxyethanol, benzyl alcohol, phenethyl alcohol, and mixtures thereof.

3. The method of claim 1, wherein the aromatic alcohol is phenoxyethanol.

4. The method of claim 1, wherein said TRPV-1 antagonist inhibits the calcium flux of the aromatic alcohol by at least about 12% as measured by the Calcium Flux Test.

5. The method of claim 1, wherein said TRPV-1 antagonist is 4-tertiary butyl cyclohexanol.

* * * * *